(12) United States Patent
Evans et al.

(10) Patent No.: US 7,375,647 B2
(45) Date of Patent: May 20, 2008

(54) METHOD AND APPARATUS FOR COMMUNICATING DATA BETWEEN A MEDICAL DEVICE AND A CENTRAL DATA REPOSITORY

(75) Inventors: Junius A. Evans, Carlsbad, CA (US); Daniel Pettus, Carlsbad, CA (US)

(73) Assignee: iMetrikus, Inc., Carlsbad, CA (US)

( * ) Notice: Subject to any disclaimer, the term of this patent is extended or adjusted under 35 U.S.C. 154(b) by 1073 days.

(21) Appl. No.: 09/977,472

(22) Filed: Oct. 15, 2001

(65) Prior Publication Data

US 2003/0072424 A1   Apr. 17, 2003

(51) Int. Cl.
*H04Q 1/00*   (2006.01)

(52) U.S. Cl. .................................. 340/825.52

(58) Field of Classification Search .................... 705/2, 705/3; 600/300, 301, 484; 710/10; 607/5; 455/419; 715/741; 755/419; 340/825.52
See application file for complete search history.

(56) References Cited

U.S. PATENT DOCUMENTS

| | | | | |
|---|---|---|---|---|
| 5,341,812 A | * | 8/1994 | Allaire et al. | 600/508 |
| 5,375,604 A | * | 12/1994 | Kelly et al. | 600/484 |
| 5,410,471 A | * | 4/1995 | Alyfuku et al. | 600/300 |
| 5,933,136 A | * | 8/1999 | Brown | 715/741 |
| 5,997,476 A | * | 12/1999 | Brown | 600/300 |
| 6,167,258 A | * | 12/2000 | Schmidt et al. | 455/419 |
| 6,168,563 B1 | * | 1/2001 | Brown | 600/301 |
| 6,223,229 B1 | * | 4/2001 | Kvamme | 710/10 |
| 6,248,065 B1 | * | 6/2001 | Brown | 600/300 |
| 7,016,726 B1 | * | 3/2006 | Picardo et al. | 607/5 |

* cited by examiner

*Primary Examiner*—Christopher L. Gilligan
*Assistant Examiner*—Dilek B. Cobanoglu
(74) *Attorney, Agent, or Firm*—BeyerWeaver LLP

(57) ABSTRACT

Methods and devices are disclosed for transmitting medical and health-related data from self-monitoring diagnostic devices via an intermediate device to a central server or data repository where the intermediate device is adaptable to numerous medical and health meters. A method of transmitting metric data from a medical data collecting device to a server computer is described. A cable type is first determined once a self-monitoring diagnostic device is connected to an intermediate data trafficking device, connected to a telephone line or a PC with Internet access. A value representing the cable type is then transmitted from the intermediate device to a server computer. The intermediate device receives diagnostic device configuration information or intelligence from the server computer. Using this intelligence, components internal to the intermediate device are then configured to enable communication between the self-monitoring device and the data repository or central server.

10 Claims, 6 Drawing Sheets

METHOD AND APPARATUS FOR COMMUNICATING DATA BETWEEN A MEDICAL DEVICE AND A CENTRAL DATA REPOSITORY

BACKGROUND OF THE INVENTION

1. Field of the Invention

The present invention relates generally to portable medical devices for collecting and storing medical data from self-diagnostic medical devices. More specifically, it relates to a device capable of collecting data from a variety of medical data gathering devices having various, non-standard interfaces and transmitting the data to a central repository via a public network.

2. Discussion of Related Art

Diagnostic markers or data, whether from home devices or from medical labs, often determine what actions are to be taken with regard to a particular health care consumer. Transmitting data from home devices to a central repository is an important component in improving health conditions and for preventive care.

Health care consumers with medical conditions should be able to communicate, from remote locations, timely information about their conditions to a doctor or to a health information service provide that maintains a central repository of data which can analyze the data and send alert messages as needed. This communication should be done accurately and should be convenient for the consumer so that it is done consistently. Specifically, individuals with chronic medical conditions must regularly collect, record, process and share information about their chronic conditions in order to develop and manage a preventative health action plan. Presently, many health care consumers manually record data from their diagnostic medical devices into a notebook or log book, for example. Such devices include blood glucose meters, digital blood pressure cuffs, spirometers, digital scales, PSA blood level testing meters, and insulin pumps among others.

Individuals who use self-monitoring diagnostic medical devices are not always near a computer and are unable to communicate their medical data to a central repository which contains a personal user health profile. Such web-based personal health records have several benefits for individuals with chronic conditions and their health care providers. One benefit is near real-time diagnostic metric data analysis in either "manual" (viewing records online) or automated formats (rule engine alerts and reminders).

Some of the barriers to providing regular diagnostic metric uploads for use on the Internet to a health information service provider that maintains a central data repository relate to connectivity and interfaces. Another barrier is the lack of an interface standard for self-monitoring devices. Manufactures of such devices have developed proprietary software protocols and physical layer connections. Some have also provided a proprietary interface cable for connecting their device to a personal computer. Thus, since no standard exists, each device uses a different cable schema and many of the manufacturers do not meet the electrical standards for RS232.

Thus, no interface standard exists for self-monitoring devices and manufacturers of such devices have developed proprietary software protocols and physical layer connections. As a result, the most common method of connecting a device to a personal computer is through a proprietary interface cable. However, since no standard exists with respect to cable design, each device model uses different cable schemas. In some cases, a single manufacturer will have numerous cables for different models of its devices. As mentioned, most of these devices do not interface with RS232-C electrical connections required by most PCs. To solve this problem, manufacturers have developed custom cables that include active components in the cable, such as Lifescan of Milpitas, Calif. or a separate interface box, such as Roche Diagnostics of Indianapolis, Ind.

Another drawback for consumers is that acquiring cables for a device is difficult, expensive and time consuming. The self-diagnosing medical device companies do not view accessories for interfacing as part of their core business. Moreover, some patients use two or three different devices, for example from those listed above, and therefore need to obtain different cables for each device. In addition, some existing devices, such as from Life Chart of Mountain View, Calif. save all metric data and protocol data on the device. However, when a new meter is added, the intelligence in the device needs to be changed thereby making the device fairly inadaptable to new metrics.

What is needed is a multi-interface appliance or component that reduces the complexities associated with cable interfaces by having a common cabling schema, such as an RS232 cable interface. The appliance should allow an individual to connect to a central repository through the web without having to use a PC or any type of internet appliance. This box should be battery powered and have one common cable connection to a PC. More significantly, such an appliance should allow the consumer to dial in via a standard telephone connection to a health information service provider without having to go through a PC to access the Internet. The appliance should also be 'multi-talented' in that it should be able to interface with various types of medical self-diagnostic devices rather than simply one type, such as blood glucose monitors. The appliance should also be adaptable in that new meters can be measured without having to adjust the internal components or intelligence in the appliance.

SUMMARY OF THE INVENTION

To achieve the foregoing, methods and apparatus are disclosed for transmitting medical and health-related data from self-monitoring diagnostic devices via an intermediate device to a central server or data repository where the intermediate device is adaptable with numerous medical and health meters. In one aspect of the present invention, a method of transmitting metric data from a medical data collecting device to a server computer is described. A cable type is first determined once a self-monitoring diagnostic device is connected to an intermediate data trafficking device. A value representing the cable type is then transmitted from the intermediate device to a server computer. The intermediate device then receives diagnostic device configuration information or intelligence from the server computer. Components internal to the intermediate device are then configured to enable communication between the intermediate device and the diagnostic medical device. Metric data is then received from the medical device and transmitted to the server computer.

In another aspect of the present invention a method of sending metric data from a self-monitoring diagnostic meter to a data repository using an intermediate device is described. A first connection between an intermediate device and a self-monitoring diagnostic meter is enabled and a second connection between the intermediate device and a host input/output is enabled. A specific type of self-monitoring diagnostic meter is determined by examining a cable type value at the data repository. The intermediate device is then configured using intelligence data sent from the data repository thereby enabling the intermediate device to receive data from the self-monitoring diagnostic meter through the first connection and transmitting the data through a second connection.

DETAILED DESCRIPTION OF THE PREFERRED EMBODIMENTS

Reference will now be made in detail to a preferred embodiment of the invention. An example of the preferred embodiment is illustrated in the accompanying drawings. While the invention will be described in conjunction with a preferred embodiment, it will be understood that it is not intended to limit the invention to one preferred embodiment. To the contrary, it is intended to cover alternatives, modifications, and equivalents as may be included within the spirit and scope of the invention as defined by the appended claims.

Figure 1:
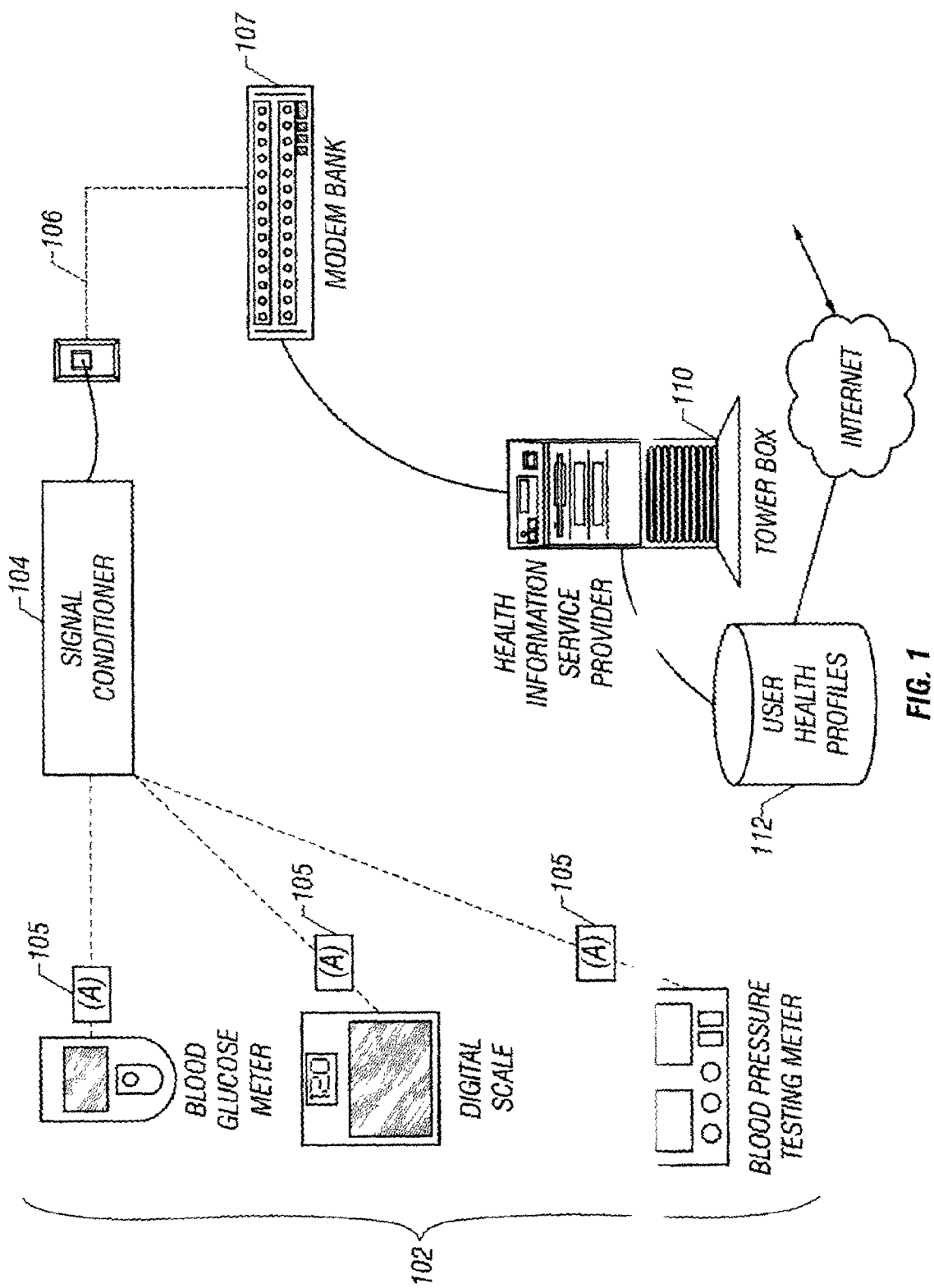
FIG. 1 is a block diagram of a configuration showing the context in which a signal conditioner is used in accordance with one embodiment of the present invention.

In accordance with a preferred embodiment of the present invention, there is provided a signal conditioner capable of trafficking metric data between a variety of self-diagnosing devices and a health information service provider ("service provider"). The service provider controls an aggregate server that contains or controls a database that in turn contains user health profiles among other data. To further illustrate the foregoing, FIG. 1 is a block diagram of a configuration showing the context in which a signal conditioner is used in accordance with one embodiment of the present invention. A number of different types of self-diagnosing medical devices 102 can interface with a signal conditioner or interface appliance 104. Device-independent appliance 104 is described in greater detail in FIG. 2 below. A signal conditioner adaptor assembly 105 is used to connect various medical devices 102 to signal conditioner 104. Adaptor assembly 105 has a receptacle in which a device-specific adaptor is inserted. The receptacle is designed to accept any type of device adaptor associated with self-diagnosing medical devices 102. Each device 102 typically comes with its own adaptor that snaps into the receptacle and each device-specific adaptor has a specific resistance. The signal conditioner also has a specific resistance. As described below, identification of the device is done by using a voltage divider and analog detect schema. The voltage divider divides the device adaptor resistance by the signal conditioner resistance to produce an analog voltage. This voltage is sent to an analog/digital converter in signal conditioner 104, described below.

In a preferred embodiment, signal conditioner 104 connects to a telephone line 106 using an internal modem (not shown). Metric data is then transmitted via a standard telephone line to a modem bank 107 that connects to the service provider which parses the data before storing it in a database 112. Server 110 also contains intelligence and other information to configure signal conditioner 104 according to the type of device 102 to which it is connected.

Figure 2:
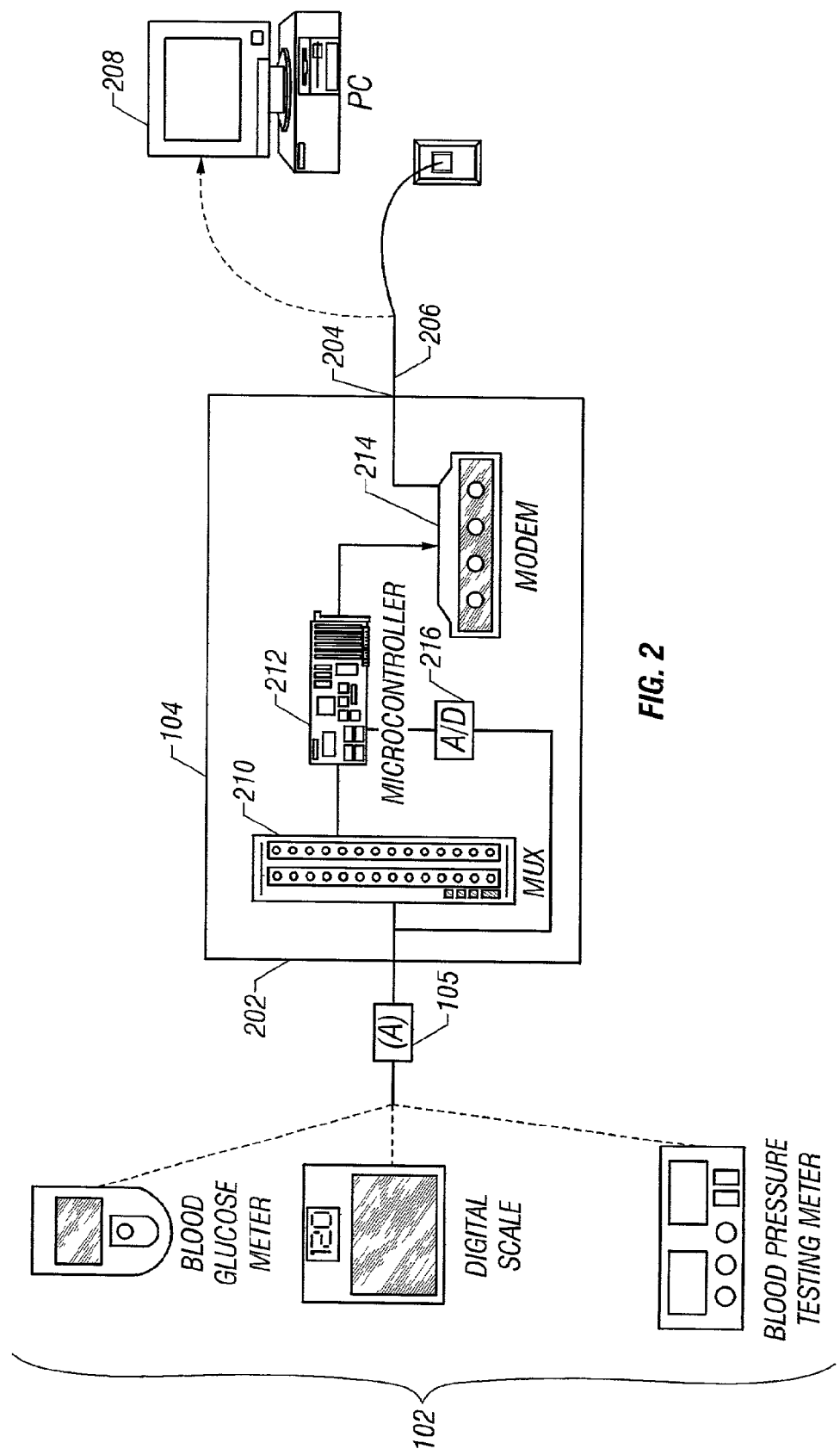
FIG. 2 is a block diagram of a signal conditioner capable of interfacing with numerous type of self-diagnosing medical devices on one end and a host device on the other in accordance with one embodiment of the present invention.

FIG. 2 is a block diagram of a signal conditioner capable of interfacing with numerous type of self-diagnosing medical devices on one end and a host device on the other in accordance with one embodiment of the present invention. A signal conditioner 104 shown in FIG. 1 has a self-diagnosing medical device I/O port 202 and a host I/O port 204. As described above, device I/O 202 can interface with numerous type of devices 102 having different interface standards and communication protocols via adaptor assembly 105. These include 5V TTL/CMOS, 3V TTL/CMOS, RS232, and IRDA. Host I/O 204 enables connections to a telephone jack 206 or to a PC 208. It is through host I/O 204 that data is communicated to and from a server under control of a service provider. In signal conditioner 104 are numerous components: a multiplexer (MUX) 210, a microcontroller 212, a modem 214; and an analog/digital converter 216, among other components not shown. MUX 210 is able to switch and communicate different voltage levels and signal levels (TTL, CMOS, RS232, or IRDA).

Signal conditioner 104 can be described as a configurable multiplexer in that all the various signal and voltage levels go through a single channel, thus a "configurable" multiplexer. Normally, the different levels would be handled by an equal number of channels. Signal conditioner 104 essentially transposes or repackages signals from various devices 102. In contrast to existing devices, signal conditioner 104 does not store or have embedded any intelligence or knowledge of devices 102 with which it can interface. This intelligence is kept on server 110 and is used to configure signal conditioner 104 according to the type of device to which it is connected. The functions of these components are described below with respect to the process that takes place with signal conditioner 104.

Figure 3:
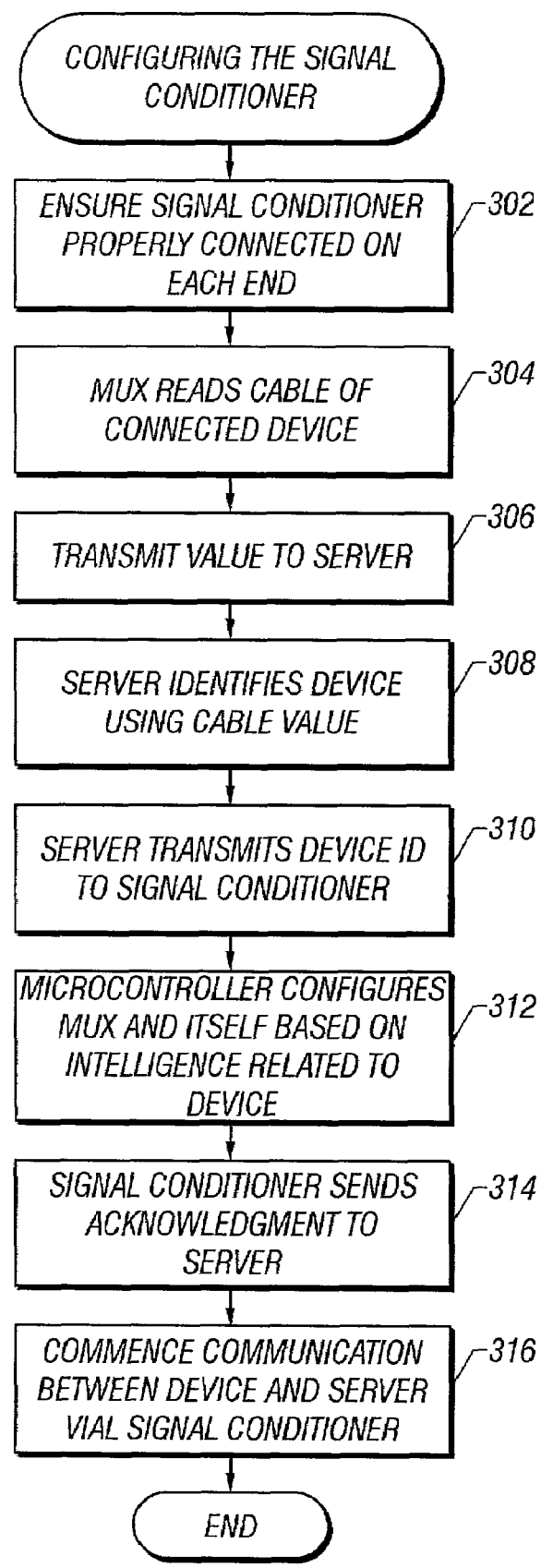
FIG. 3 is a flow diagram of a process of configuring the signal conditioner to communicate data between a particular self-monitoring medical device and a service provider in accordance with one embodiment of the present invention.

FIG. 3 is a flow diagram of a process of configuring the signal conditioner to communicate data between a particular self-monitoring medical device and a service provider in accordance with one embodiment of the present invention. In the preferred embodiment, the signal conditioner sends metric data directly through a dial-up modem via a standard public telephone switch network to a service provider server. As described above, the signal conditioner can also be used with a PC to access the Internet and communicate with the server. First, a health care consumer or healthcare-taker plugs in a self-monitoring device to the signal conditioner through device I/O port 202. Host I/O 204 is connected to a telephone line. At step 302 the signal conditioner determines whether it is properly connected on each side. If the device is not connected to the device I/O or the host I/O is not connected to a telephone line, it does not begin operation. The signal conditioner uses a series of LED indicators for each step of the upload operation. Both successful and error states are indicated using the LEDs. At step 304 the MUX reads the cable, represented by a particular value, that is plugged into the signal conditioner. This is described in greater detail in FIG. 4 below. Once a value representing the type of cable is determined, this value is transmitted to the server via the telephone line at step 306. Examples of device cable types are: ⅛"Audio Plug, ³⁄₃₂"Audio Plug, Custom 3 PIN PCB, and Custom 3 PIN, among others.

The server at the service provider uses this value to identify the device connected to the signal conditioner at step 308. The signal conditioner identifies the attached device using a voltage divider schema. Basically a fixed resistor value is located on the signal conditioner main circuit board. Each device cable adaptor contains a unique resistor value. Dividing the voltage and obtaining the analog value determines the unique device connector to the signal conditioner. At step 310 a device identifier is sent to the signal conditioner. Specifically, microcontroller 312 receives the device ID at step 310. At step 312, the microcontroller switches the MUX to the appropriate output levels and configures itself to the appropriate bit rate. At step 314 the signal conditioner sends a positive acknowledgment to the server that it has received and processed the device ID. This acknowledgment can also be sent before switching the MUX or configuring the microcontroller. At step 316 communication begins between the device and the server via the signal conditioner. At this stage, metric data from the device is uploaded to the server and the process is complete. The amount of time this takes depends on various factors known in the field such as amount of data stored in memory and bit rate. As mentioned above, signal conditioner 104 does not keep any data regarding any of the dozens of devices with which it can interface. All the intelligence for configuring it is sent essentially on a 'need-to-know' basis from the server. One of the numerous advantages of this is that the signal conditioner is adaptable to future devices; all that needs to be done is to store intelligence for the new device on the service provider server.

Figure 4:
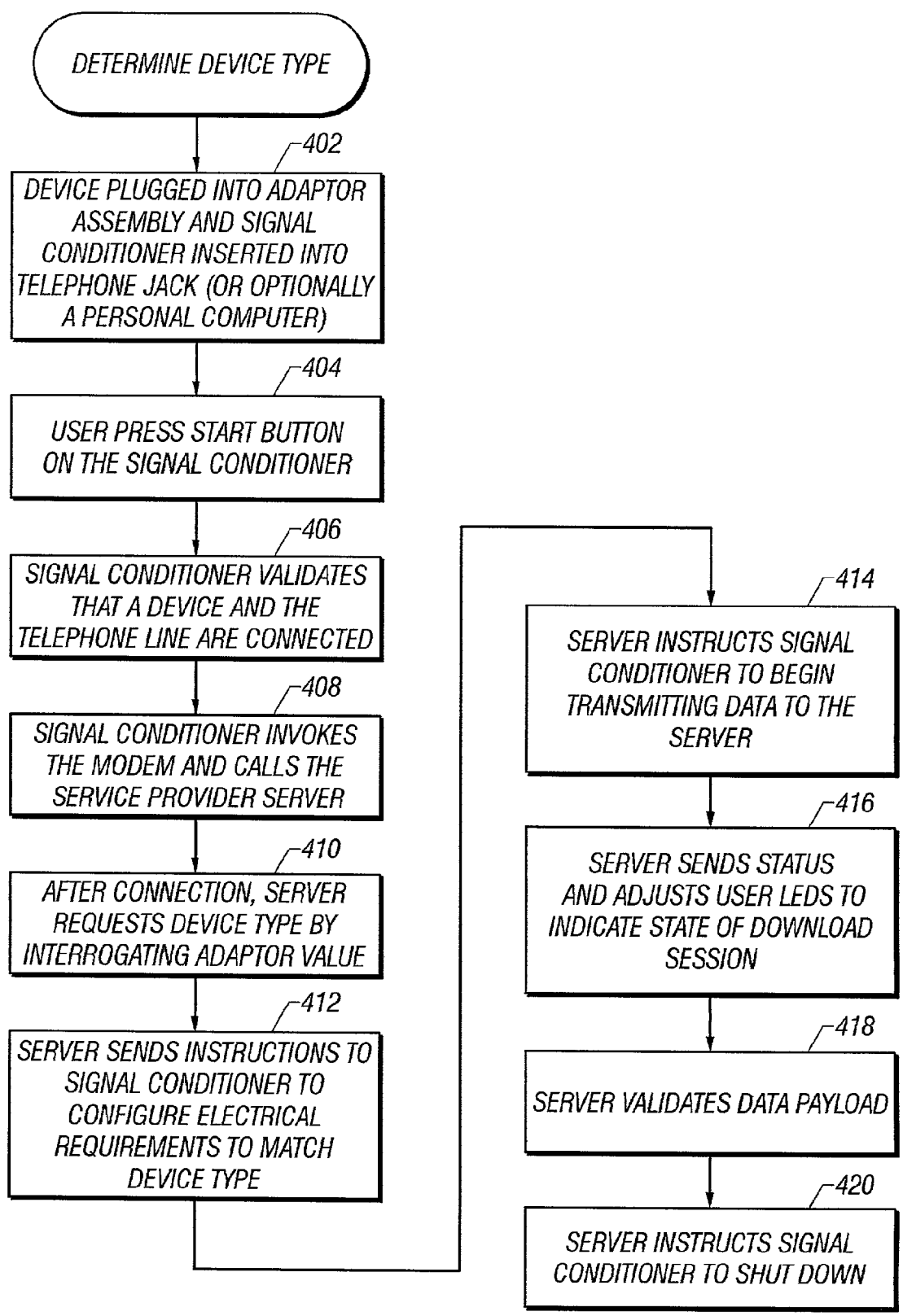
FIG. 4 is a flow diagram of a process of determining the type of cable connected to the signal conditioner in accordance with one embodiment of the present invention.

FIG. 4 is a flow diagram of a process of determining the type of cable connected to the signal conditioner in accordance with one embodiment of the present invention. It describes in greater detail a process by the signal conditioner in determining the type of cable connected to it from the device in step 304 above. At step 402 the device adaptor is inserted into the adaptor assembly thereby allowing the adaptor assembly to plug into the device. The signal conditioner is plugged into a telephone jack or a personal computer. At step 404 the user presses a START button on the signal conditioner. At step 406 the signal conditioner validates that the device is connected to the signal conditioner via the adaptor assembly and that the signal conditioner is connected to a telephone jack. This is done once the two connections to the signal conditioner are in place. At step 408 the signal conditioner invokes an internal modem 214 and dials into the service provider server. At this time a handshake is performed between the signal conditioner and the modem bank using known techniques.

Once a connection is established between the signal conditioner and the server, at step 410 the server obtains the device type by interrogating an adaptor value. At step 412 the server sends instructions to the signal conditioner to configure its electrical requirements to match the device type. This configuration can be according to RS232, 5 volt, 3 volt, and so on. At step 414 the server instructs the signal conditioner to begin transmitting data from the device to the server. The server then parses the metric data from the self-monitoring device and stores it in a user health profile for the user in a database under control of the service provider. At step 416 the server sends status data and adjusts LEDs on the signal conditioner to indicate the state of the download session. At step 418 the server validates the data it received from the signal conditioner. At step 420 the server instructs the signal conditioner to shut down and the connection is terminated.

Figure 5:
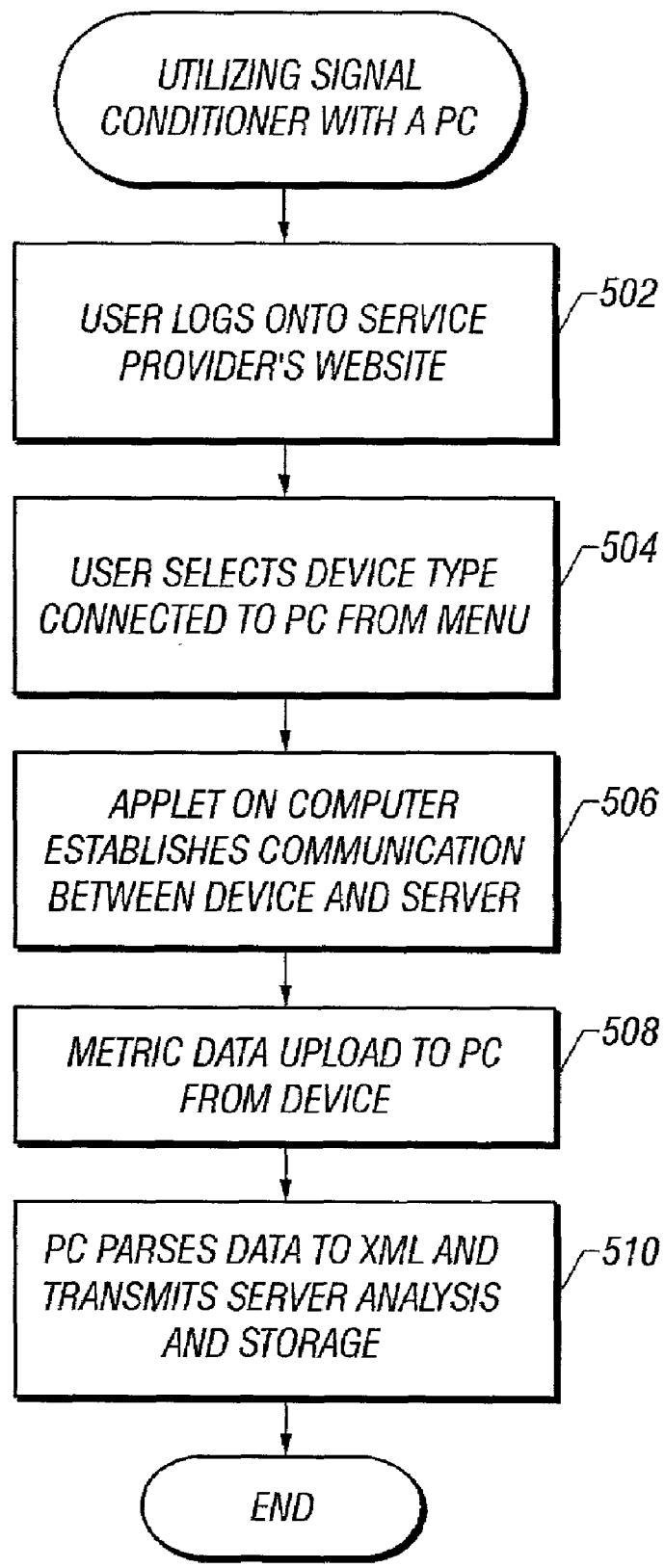
FIG. 5 is a flow diagram of a process of utilizing the signal conditioner with a personal computer to upload metric data to a server in accordance with one embodiment of the present invention.

FIG. 5 is a flow diagram of a process of utilizing the signal conditioner with a personal computer to upload metric data to a server in accordance with one embodiment of the present invention. At step 502 a health care consumer logs onto the service provider web site using a computer or Internet appliance. The consumer healthcare-taker will have access to a personal health profile that contains health and wellness data that has been collected about the user. It is assumed that the service provider has some information about the user, such as which self-monitoring devices the user is likely to utilize. At step 504 the user opens a pull-down menu or other type of menu from which the user can choose the type of device that is connected to the computer. Such a menu would normally be customized to the user. At step 506, an applet on the computer provided by the service provider establishes communication between the device and the server. The applet used to establish this communication depends on the type of self-monitoring device and associated protocol used by the device. Thus, a computer may have several different applets depending on the number of devices used by the consumer. At step 508 the user invokes the metric data upload or data dump wherein the device transmits all its data to the computer. At step 510 the computer parses the metric data into XML form and transmits the data to the server where the data is analyzed and stored in the user's health profile.

Figure 6:
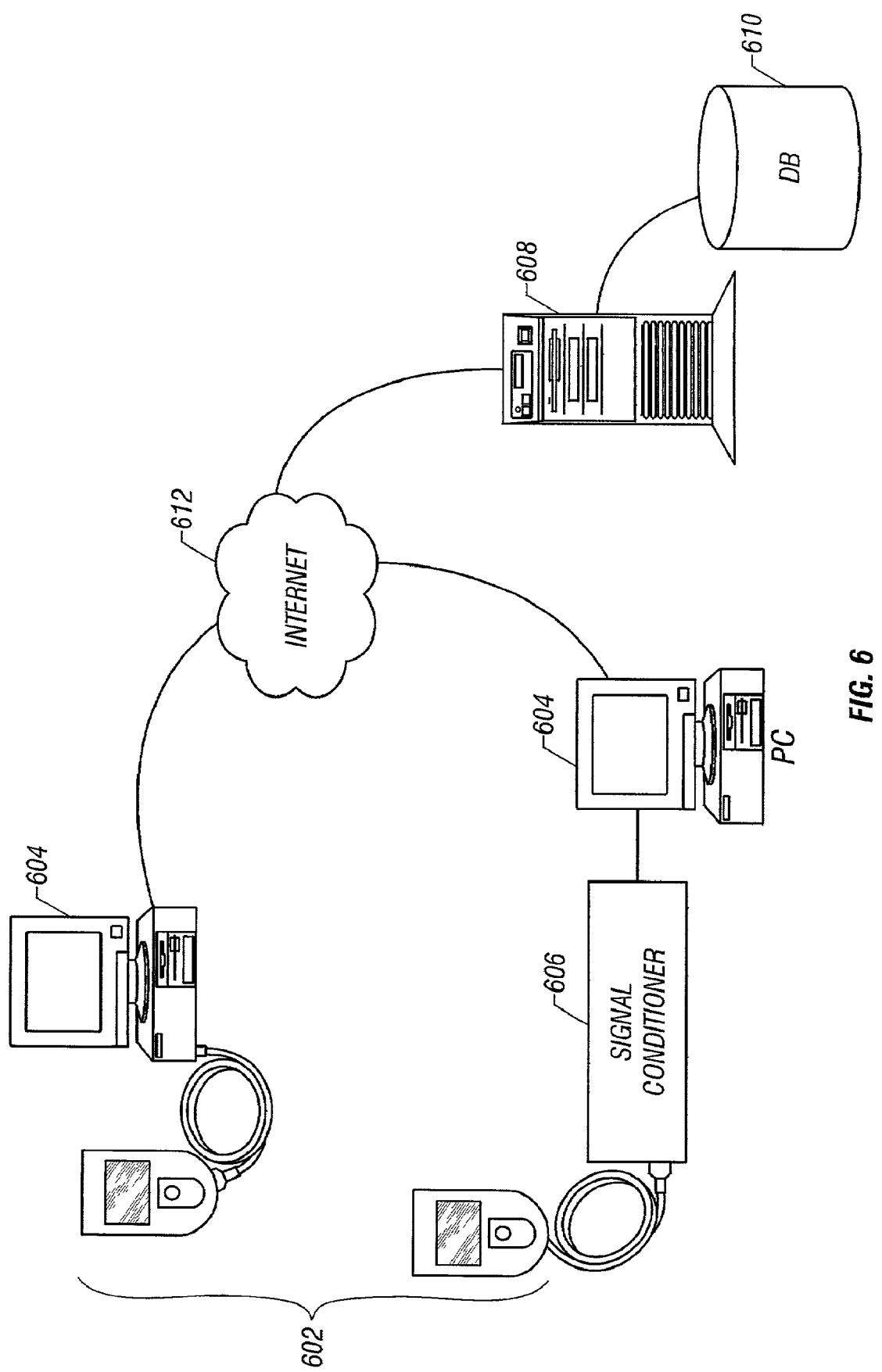
FIG. 6 is a block diagram showing two computer-based configurations for transmitting metric data to a service provider server in accordance with one embodiment of the present invention.

A signal conditioner can also be used in the computer configuration model. The modification made is that the menu at step 504 includes the option to use the signal conditioner instead of selecting the self-monitoring device directly. The signal conditioner is then used to collect the data from the device as described above and the data is then transmitted to the computer from where it is uploaded to the server. FIG. 6 is a block diagram showing both configurations. In the configuration described in FIG. 5, a self-monitoring device 602 is connected directly to a PC 604. In a preferred configuration, device 602 is connected to a signal conditioner 606. A self-monitoring device 602 is connected to a signal conditioner 606 in a manner described above. The host I/O component of signal conditioner 606 is then connected directly to a serial port of computer 604 instead of going directly to a phone line. From computer 604 data is uploaded to server 608 via the Internet 612 and modem bank 107. From server 608 the metric data is downloaded to database 610.

Although the foregoing invention has been described in some detail for purposes of clarity of understanding, it will be apparent that certain changes and modifications may be practiced within the scope of the appended claims. Furthermore, it should be noted that there are alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.

The invention claimed is:

1. A method of transmitting metric data from a medical data collecting device having a unique resistor value via an intermediate device having a fixed resistor value to a server computer, the method comprising:

receiving the unique resistor value from the medical data collecting device;

determining a cable type of a medical data collecting device by dividing the fixed resistor value by the unique resistor value of the intermediate device, thereby deriving an analog value;

transmitting a cable type value corresponding to the cable type to a server computer;

receiving device configuration instructions from the server computer, the server computer using the cable type value to identify the medical data collecting device and storing configuration data for a plurality of medical devices;

configuring a multiplexer in the intermediate device to an appropriate output level and to an appropriate bit rate to enable communication with the medical data collecting device; and receiving metric data from the medical data collecting device at the intermediate device for transmission to the server computer.

2. A method as recited in claim 1 wherein receiving device configuration instructions from the server computer further comprises:

on the server computer, using the cable type value to retrieve the device configuration instructions from a database such that intelligence regarding the medical data collecting device resides on the server computer.

3. A method as recited in claim 1 further comprising:

determining whether a host input/output connection is enabled and a device input/output is enabled.

4. A method as recited in claim 1 further comprising:

the multiplexer reading the cable of the medical data collecting device; and a modem transmitting the cable type value to the server computer wherein a predetermined dial-up number is used to connect to the server computer.

5. A method as recited in claim 1 further comprising transmitting an acknowledgment to the server computer.

6. A method of sending metric data from a self-monitoring diagnostic meter to a data repository using an intermediate device with an adaptor assembly, the method comprising:

enabling a first connection between the intermediate device and a self-monitoring diagnostic meter via the adaptor assembly and enabling a second connection between the intermediate device and a host input/output;

determining a specific type of self-monitoring diagnostic meter by examining at the data repository a cable type value by dividing a unique resistor value of the diagnostic meter and a fixed resistor value of the intermediate device to derive an analog value; and configuring a multiplexer in the intermediate device using intelligence data sent from the data repository, wherein the multiplexer is configured to an appropriate output level and to an appropriate bit rate;

receiving data via the adaptor assembly from the self-monitoring diagnostic meter through the first connection; and transmitting the data through a second connection, wherein the intermediate device performs only as a conduit for the data.

7. A method as recited in claim 6 further comprising reconfiguring the intermediate device with new intelligence data when a different self-monitoring diagnostic meter is connected to the intermediate device.

8. A method as recited in claim 6 further comprising directly connecting the intermediate device to a telephone connection for transmitting metric data to the data repository.

9. A method as recited in claim 6 further comprising directly connecting the intermediate device to one of a plurality of self-monitoring diagnostic meters.

10. A method as recited in claim 6 further comprising installing a second a intelligence data in the central repository to accommodate a new, previously unknown, self monitoring diagnostic meter.

* * * * *